United States Patent [19]

Edison et al.

[11] 4,031,154

[45] June 21, 1977

[54] BENZENE BY HYDROGENATIVE DEALKYLATION

[75] Inventors: Robert Raynold Edison, Olympia Fields; Thorpe Dresser, Markham, both of Ill.

[73] Assignee: Atlantic Richfield Company, Los Angeles, Calif.

[22] Filed: Sept. 15, 1975

[21] Appl. No.: 613,379

[52] U.S. Cl. .................... 260/672 R; 260/672 NC
[51] Int. Cl.² ......................................... C07C 3/58
[58] Field of Search ............... 260/672 NC, 672 R

[56] References Cited

UNITED STATES PATENTS

| 3,296,323 | 1/1967 | Myers et al. | 260/672 R |
| 3,401,209 | 9/1968 | Majewski | 260/672 R |
| 3,927,136 | 12/1975 | Suggitt et al. | 260/672 NC |

FOREIGN PATENTS OR APPLICATIONS

| 1,195,988 | 6/1970 | United Kingdom | 260/672 R |

*Primary Examiner*—C. Davis
*Attorney, Agent, or Firm*—John R. Ewbank

[57] ABSTRACT

In a process in which a hydrocarbon stream is hydrogenatively dealkylated to prepare benzene, small amounts of naphthalene may occur in the crude product. Instead of isolating and recovering such naphthalene, it is recycled to extinction so that the process comprises the hydrogenative conversion of the minor amount of naphthalene to benzene and methane.

10 Claims, No Drawings

BENZENE BY HYDROGENATIVE DEALKYLATION

FIELD OF INVENTION

The invention relates to preparing benzene by the hydrogenative dealkylation of hydrocarbon streams consisting predominantly of alkylated mononuclear aromatic hydrocarbon.

PRIOR ART

Fiegelman U.S. Pat. No. 3,160,671 describes a method of hydrodealkylation in which a small amount of biphenyl enhances the yield of mononuclear aromatic product. Hariu 3,101,380 describes a hydrodealkylation method in which the recycle hydrogen is purified to remove propylene, ethylene, and methane by solvent extraction in a large amount of recirculated aromatic hydrocarbon product. Significant amounts of methane and lower boiling hydrocarbons are formed in a hydrogenative dealkylation zone. The purification of the recycle hydrogen represents one of the costly engineering requirements for a hydrodealkylation method. At the high pressure employed in the hydrodealkylation zone, relatively little hydrogen but significant amounts of lower alkyl hydrocarbons such as methane can be dissolved in the aromatic product. When such solution of the hydrocarbons in the pressurized aromatic hydrocarbon is transferred to a low pressure separator, the methane and related hydrocarbons and the small amount of dissolved hydrogen are volatilized, so that the recirculating solvent satisfactorily extracts the methane from the hydrogen so that the purity of the hydrogen recycled to the hydrodealkylation zone can be maintained satisfactorily.

The manufacture of naphthalene from alkyl naphthalenes in a hydrodealkylation zone is very similar to the hydrogenative dealkylation of xylene to form benzene. Moreover, a wide boiling feedstock can be dealkylated to prepare both benzene and naphthalene simultaneously. Such simultaneous production of naphthalene by dealkylation of alkyl naphthalenes and the preparation of benzene by dealkylation of alkyl benzenes is a process which has been previously proposed. Distillation facilities for separating napthalene product from benzene product has been a standard feature for a dealkylation plant employing a benzene precursor feedstock sufficiently high boiling to include significant amounts of naphthalene precursors, for example, containing more than about 10 percent boiling above the 217° C. boiling point of naphthalene.

In the processing of feedstocks containing components boiling above the 144° C. boiling point of orthoxylene, and particularly in the processing of feedstocks containing butyl benzene (b.p. 180°), or orthodiethyl benzene (b.p. 184° C.), or related precursors, naphthalene can be formed from alkylated benzene notwithstanding the absence of naphthalene from the initial feedstock. It has been the custom to design plants to include distillation facilities for the separation of the naphthalene product from the crude product stream whenever the plant was designed to handle feedstocks containing more than trace amounts of the relatively high boiling precursors for naphthalene.

Naphthalene is a solid at room temperature and can readily condense in cool portions of vapor streams containing a mixture of benzene and naphthalene vapor. Chemical engineers have learned about the problems resulting from the unintended accumulation of naphthalene in vapor lines comprising benzene and naphthalene. Chemical engineers have emphasized the importance of providing appropriate separation facilities rather than to assume the risks inherent in providing conduits for streams in which naphthalene blockage might occur. In order to provide absolute assurance of freedom from condensation of naphthalene in a conduit carrying about equal amounts of naphthalene vapor and benzene vapor, the conduit walls must be heated hotter than for reliable functioning of a conduit carrying only benzene vapor. Chemical engineers are familiar with the problems connected with externally heated and/or specially insulated conduits and take numerous precautions to avoid approaching conditions possibly requiring such specialized conduits.

SUMMARY OF INVENTION

In accordance with the present invention, a feedstock containing a minor amount of high boiling components (e.g., above about 177° C.) is converted to benzene by hydrodealkylation, all of the naphthalene formed in the hydrodealkylation being recycled to the hydrodealkylation zone for conversion to benzene.

The concentration of naphthalene in the total feed to the hydrodealkylation zone is less than 10 percent of the liquid hydrocarbon feed. By staying below such 10 percent maximum, the naphthalene can be exhaustively converted to benzene. Naphthalene is not as readily converted to benzene in a hydrodealkylation zone as is a compound such as toluene. The present invention includes the discovery that as long as the concentration of the naphthalene is small, such naphthalene can be exhaustively recycled to form benzene. In some instances, the naphthalene may be formed, not by dealkylation of an alkylated naphthalene such as methyl naphthalene, but by the conversion of an alkyl benzene such as orthodiethylbenzene in the hydrodealkylation zone. It has been found that orthodiethylbenzene can undergo reactions such as the formation of ortho divinyl benzene which can react in the hydrodealkylation zone to form naphthalene. Similarly, butyl benzene, orthopropyl toluene, and related hydrocarbons can form naphthalene in a hydrodealkylation zone. Moreover, reactive fragments resembling ethylene radicals, propylene radicals etc. can combine with various mononuclear aromatic compounds to provide naphthalene or precursors for naphthalene at dealkylation conditions. Thus, naphthalene can build up to a measurable concentration in hydrodealkylating a fresh feedstock having an end boiling point embracing $C_9$ aromatic and nominally excluding $C_{10}$ aromatics.

Advantages are achieved by conducting the hydrodealkylation at an elevated pressure and temperature in the absence of a catalyst. If desired a catalytic hydrodealkylation process may be employed. The present invention is concerned primarily with the exhaustive recycling of the naphthalene to form benzene. The initial feedstock is desirably controlled to contain sufficiently small amounts of components boiling about 179° C. that the equilibrium concentration of naphthalene in the total hydrocarbon feed is less than 10 percent by weight, ordinarily less than 5 percent, and desirably less than about 2 percent by weight.

The invention is further clarified by reference to a plurality of examples.

EXAMPLE 1

A fresh feedstock stream has a composition, expressed in terms of pound mols per hour, as follows:

| | |
|---|---|
| cyclopentane, etc. | 61.7 |
| benzene | 164.0 |
| toluene | 84.0 |
| xylenes | 48.8 |
| ethylbenzenes | 33.7 |
| $C_9$ aromatics | 10.0 |
| naphthalene | 10.4 |
| Total | 412.6 |

Such fresh feed is mixed with a recycle consisting essentially of:

| | |
|---|---|
| benzene | 0.4 |
| toluene | 31.7 |
| xylenes | 2.7 |
| ethylbenzene | 1.9 |
| $C_9$ aromatics | 0.5 |
| naphthalene | 10.0 |
| biphenyl | 6.8 |
| Total | 54.0 |
| Total feedstock | 466.6 |

The total feedstock has a composition consisting of:

| | No. mols/hr. | % |
|---|---|---|
| Cyclopentane, etc. | 61.7 | 13.2 |
| Benzene | 164.4 | 35.3 |
| Toluene | 115.7 | 24.8 |
| Xylenes | 51.5 | 11.1 |
| Ethyl benzene | 35.6 | 7.6 |
| $C_9$ aromatics | 10.5 | 2.2 |
| Naphthalene | 20.4 | 4.4 |
| Biphenyl | 6.8 | 1.4 |
| Total | 466.6 | 100.0 |

Such feedstock is subjected to the hydrodealkylation zone to prepare benzene.

The product consists of 335.7 pound mols per hour of benzene, corresponding to about a 72 percent molar yield of total feedstock or 81.6 molar percent yield based upon fresh feedstock. About 3.9 pound mols per hour of heavy material is purged from the crude product prior to the recycling of the liquid hydrocarbon, but such heavy material does not include significant amounts of naphthalene. The end boiling point of the recycle stream is about 220° C., thus including the naphthalene having a 217° C. boiling point. Because the cut point for separating the recycle stream from the heavy material is about 220° C., the ultimate rate of production of benzene is higher than when the cut point is sufficiently low to exclude naphthalene from the recycle stream. If the fresh feed is substantially free from naphthalene and if the cut point for the recycle stream just low enough to prevent the recycling of naphthalene, then the benzene production is about 333.7 pound mols per hour, or 2 pound mols per hours less than with exhaustive recycling of naphthalene. A benzene yield increase of about 0.6 percent is thus achieved by recycling naphthalene to extinction. At appropriate conditions, the increase in molar yield of benzene closely approaches the molar concentration of naphthalenes in the reactant stream.

By a series of tests, it is shown that advantages accrue from restricting the total reactor feed to contain a measureable amount but less than 10 percent by weight of naphthalene. In general, it is desirable to apply naphthalene concentration limits for fresh feed which are significantly lower than those applicable to reactor feed, inasmuch as some of the naphthalene is formed in the hydrodealkylation zone from lower boiling precursors. Adequate flexibility concerning recycle composition is manageable when the initial feedstock has a low concentration of precursors convertible to naphthalene. The concentration of naphthalene and alkyl naphthalenes should be small in the fresh feed and must be less than about 10 percent in the total reactor feed. Naphthalene concentrations in the reactor feed of up to about 10 percent can be converted to benzene by the exhaustive recycling feature of the present invention. Hydrodealkylation conditions severe enough to assure rapid and exhaustive dealkylation of toluene to benzene are severe enough to assure consumption of naphthalene if the naphthalene concentration in the reactor feed is less than about 10 percent by weight, usually less than 5 percent, desirably less than 2 percent and usually more than 0.1 percent.

EXAMPLE 2

A hydrocarbon stream is solvent extracted to provide a predominantly aromatics fraction scheduled for benzene production, and the fraction boiling between 75° C. and 230° C. is employed as fresh feedstock. Such fraction is treated as a $C_6$–$C_{10}$ aromatics hydrocarbon stream. Xylene sometimes sells for a higher price per mol than benzene. Hence, it is sometimes profitable to remove a zylene cut (b.p. 135°–150° C.) from both fresh feed and recycle. By processing a mixture rich in toluene and $C_9$ aromatics through the hydrodealkylation zone, the high price of benzene relative to the lower price per pound mol of $C_9$ aromatics and toluene provides additional economic incentives for the hydrodealkylation operation under some marketing conditions. It is sometimes profitable to process some $C_{10}$ aromatics along with the $C_9$ aromatics.

The aromatic hydrocarbon stream comprising components boiling about as low as 75° C. and higher boiling aromatic $C_9$ components, the end boiling point being within a range from about 180° to about as high as 230° C. is directed to a hydrodealkylation zone containing a chromia-alumina catalyst.

The hydrogen to aromatic hydrocarbon ratio is maintained within a range from about 5/1 to about 20/1 at a pressure of from about 5 to about 50 atmospheres. It is desirable to minimize the concentration of aliphatic hydrocarbons (e.g., methane), in the hydrogen stream, but the $H_2$/aromatic hydrocarbon ratios are discussed as significant while treating the aliphatic hydrocarbons as quasi-inert diluents. The temperature of the hydrodealkylation zone is maintained within a range from 400° C. to 800° C., desirably about 600° C. Space rates within a range from about 0.1 to about 10 volumes of liquid hydrocarbon per volume of reaction zone per hour are appropriate desirably from about 1 to about 3 LHSV.

By a series of tests it is established that the total feed should contain some naphthalene, usually at least 0.1 percent, desirably less than 2 percent, and usually less than 5 percent, but the exhaustive recycling appears to be manageable up to about 10 weight percent naphthalene.

An aromatic hydrocarbon stream having a 75°–230° C. boiling point range is mixed with a recycle stream and the mixture is distilled to remove a 135°–145° C. xylene heart cut. Such aromatic stream is modified by the addition of toluene and mesitylene so that it consists of about 35 percent toluene and 35 percent mesitylene and 30 percent miscellaneous hydrocarbons. Such stream is vaporized and mixed with hydrogen to provide a 10 to 1 hydrogen to aromatic hydrocarbon ratio and directed into a hydrodealkylation zone containing a mixture of rhenium and platinum (total noble metal about 0.7 percent) on a cracking catalyst support comprising about 15 to 30 percent hydrogen faujasite in an aluminosilicate matrix (e.g., derived from kaolin or from a silica-alumina gel) having adequate porosity for a mixture of $C_{10}$ aromatic hydrocarbons for hydrodealkylation at a temperature of about 600° C. and atmospheric pressure at a LHSV of about 1. The effluent is cooled and the hydrogen is purified for recycling. The benzene product is stripped from the liquid effluent, and a bottoms fraction boiling above about 220° C. is withdrawn as a by-product, and the 82°–220° C. is recycled for admixture with said 75°–230° C. aromatic hydrocarbon fresh feed. Because the naphthalene is exhaustively recycled, the ultimate yield of xylene and benzene is about 5 percent greater than when the cut point for the recycle stream is sufficiently low to prevent such recycling of naphthalene.

Various modifications of the invention are possible without departing from the concept of the present invention as defined in the claims.

It is claimed:

1. In the method in which a fresh feedstock consisting predominantly of aromatic hydrocarbon stream having a boiling point range within the range from 75° C to 230° C, is subjected to hydrodealkylation in a hydrodealkylation zone to prepare lower boiling normally liquid products of the group consisting of xylene, toluene, and benzene, the improvement which consists of recycling to extinction the naphthalene content of the crude reaction stream, whereby some of the recycled naphthalene is converted in the hydrodealkylation zone to products of said group of xylene, toluene, and benzene, the concentration of naphthalene in the total feedstock comprising recycle and fresh feedstock being maintained at a concentration less than about 10 percent by weight of total feedstock.

2. The method of claim 1 in which the hydrogen to hydrocarbon ratio is maintained within a range from 1 to 1 to 10 to 1 in said hydrodealkylation zone.

3. The method of claim 1 in which the temperature of said hydrodealkylation zone is within the range from about 400° C to about 800° C and in which said fresh feedstock contains small amounts of naphthalene.

4. The method of claim 3 in which the temperature is about 600° C and said fresh feedstock consists predominantly of alkylated mononuclear aromatic hydrocarbons.

5. The method of claim 1 in which said hydrodealkylation zone is free from components exerting a significant catalytic action.

6. The method of claim 1 in which said hydrodealkylation zone contains a catalyst selected from the group consisting of supported chromium oxide and supported noble metal catalysts.

7. The method of claim 1 in which the cut point for said stream recycled for admixture with fresh feed is at least 217° C. but less than about 230° C.

8. The method of claim 1 in which the yield of benzene is measurably greater than in otherwise similar operations employing a cut point for the recycled stream low enough to assure a recycle stream substantially free from naphthalene.

9. The method of claim 1 in which the concentration of naphthalene in the mixture of recycle and fresh feedstock is maintained below about 5 percent.

10. The method of claim 1 in which the concentration of naphthalene in the mixture of recycle and fresh feedstock is maintained below about 2 percent.

* * * * *